US010226215B2

(12) United States Patent
Cohrs et al.

(10) Patent No.: US 10,226,215 B2
(45) Date of Patent: Mar. 12, 2019

(54) CABLE MANAGEMENT FEATURE FOR WEARABLE MEDICAL MONITOR

(71) Applicant: COVIDIEN LP, Mansfield, MA (US)

(72) Inventors: Kristine M. Cohrs, Westminster, CO (US); David P. Besko, Thornton, CO (US); Ryan M. Miller, Broomfield, CO (US); Jenna Dancy, Longmont, CO (US); Loren L. Lohrman, Thornton, CO (US)

(73) Assignee: Covidien LP, Mansfield, MA (US)

( * ) Notice: Subject to any disclaimer, the term of this patent is extended or adjusted under 35 U.S.C. 154(b) by 371 days.

(21) Appl. No.: 15/247,583

(22) Filed: Aug. 25, 2016

(65) Prior Publication Data

US 2017/0055905 A1 Mar. 2, 2017

Related U.S. Application Data

(60) Provisional application No. 62/211,399, filed on Aug. 28, 2015.

(51) Int. Cl.
*A61B 5/1455* (2006.01)
*A61B 5/00* (2006.01)
*A61B 5/024* (2006.01)

(52) U.S. Cl.
CPC ........ *A61B 5/6831* (2013.01); *A61B 5/02416* (2013.01); *A61B 5/14552* (2013.01); *A61B 5/681* (2013.01); *A61B 5/6824* (2013.01); *A61B 5/6826* (2013.01); *A61B 2562/222* (2013.01)

(58) Field of Classification Search
CPC .............. A61B 5/0205; A61B 5/14551; A61B 5/14552; A61B 5/6831; A61B 5/6824; A61B 5/6826; A61B 5/02416; A61B 5/681

See application file for complete search history.

(56) References Cited

U.S. PATENT DOCUMENTS

| 4,862,896 | A |   | 9/1989 | Reinhold, Jr. et al. |
|---|---|---|---|---|
| 5,735,800 | A | * | 4/1998 | Yasukawa .......... A61B 5/02438 600/310 |
| 5,766,131 | A | * | 6/1998 | Kondo ............... A61B 5/02416 600/310 |

(Continued)

FOREIGN PATENT DOCUMENTS

| JP | 2005110816 A | 4/2005 |
|---|---|---|
| JP | 2007117641 A | 5/2007 |

(Continued)

OTHER PUBLICATIONS

International Search Report and Written Opinion for PCT Application No. PCT/US2016/048970 dated Nov. 25, 2016; 11 pgs.

*Primary Examiner* — Eric Winakur
*Assistant Examiner* — Chu Chuan (JJ) Liu
(74) *Attorney, Agent, or Firm* — Fletcher Yoder PC

(57) ABSTRACT

A coupling portion of a wearable medical monitor may include an attachment member configured to reversibly couple the coupling portion to a body portion of the wearable medical monitor. The wearable medical monitor may be coupled to a sensor via a cable. The coupling portion may also include a cable retention feature including a channel configured to receive the cable. The cable retention feature may be configured to apply a retaining force to the cable when the cable is disposed in the channel.

23 Claims, 6 Drawing Sheets

(56) References Cited

U.S. PATENT DOCUMENTS

| | | | |
|---|---|---|---|
| 6,095,984 A | 8/2000 | Amano et al. | |
| 6,293,915 B1 | 9/2001 | Amano et al. | |
| 6,541,756 B2 | 4/2003 | Schulz et al. | |
| 6,606,512 B2 * | 8/2003 | Muz | A61B 5/14552 600/322 |
| 6,816,266 B2 | 11/2004 | Varshneya et al. | |
| 6,909,912 B2 | 6/2005 | Melker | |
| 7,127,278 B2 | 10/2006 | Melker et al. | |
| 7,220,220 B2 | 5/2007 | Stubbs et al. | |
| 7,486,979 B2 | 2/2009 | Matlock | |
| 2002/0095076 A1 * | 7/2002 | Krausman | A61B 5/14552 600/323 |
| 2002/0198443 A1 * | 12/2002 | Ting | A61B 5/021 600/323 |
| 2003/0181798 A1 * | 9/2003 | Al-Ali | A61B 5/02438 600/324 |
| 2005/0143670 A1 | 6/2005 | Umeda et al. | |
| 2007/0027375 A1 | 2/2007 | Melker et al. | |
| 2007/0038050 A1 * | 2/2007 | Sarussi | A61B 5/14552 600/324 |
| 2007/0118028 A1 * | 5/2007 | Kitajima | A61B 5/11 600/310 |
| 2007/0123756 A1 | 5/2007 | Kitajima et al. | |
| 2007/0276273 A1 | 11/2007 | Watson, Jr. | |
| 2008/0076995 A1 | 3/2008 | Hoarau | |
| 2008/0208011 A1 | 8/2008 | Shuler | |
| 2008/0281168 A1 | 11/2008 | Gibson et al. | |
| 2012/0165688 A1 * | 6/2012 | Liu | A61B 5/0006 600/500 |
| 2014/0221797 A1 * | 8/2014 | Bailey | A61B 5/0002 600/324 |
| 2015/0065832 A1 * | 3/2015 | Manion | A61B 5/746 600/340 |
| 2015/0112151 A1 | 4/2015 | Muhsin et al. | |

FOREIGN PATENT DOCUMENTS

| | | |
|---|---|---|
| JP | 2007167183 A | 7/2007 |
| JP | 2007190122 A | 8/2007 |
| JP | 2009011850 A | 1/2009 |
| WO | 2006005169 A1 | 1/2006 |

* cited by examiner

CABLE MANAGEMENT FEATURE FOR WEARABLE MEDICAL MONITOR

CROSS-REFERENCE TO RELATED APPLICATIONS

The present application claims priority to and the benefit of U.S. Provisional Application No. 62/211,399, which was filed on Aug. 28, 2015, and entitled "Cable Management Feature for Wearable Medical Monitor," the disclosure of which is hereby incorporated by reference in its entirety for all purposes.

BACKGROUND

The present disclosure relates generally to medical devices and, more particularly, to wearable medical monitors for monitoring physiological parameters of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

A wearable medical monitor is a device worn on the body of a patient that is able to capture data about the patient's physiology to allow caregivers to monitor a patient's clinical condition. A variety of types of wearable medical monitors may implement a variety of monitoring techniques, such as photoplethysmography, pulse oximetry, regional saturation oximetry, heart rate, electrocardiography (ECG), electroencephalography (EEG), electromyography (EMG), and glucose/insulin concentration monitoring. In some situations, a wearable medical monitor may be used in conjunction with one or more sensors to facilitate various monitoring techniques. For example, a wearable medical monitor may be coupled to a sensor via a cable, and the sensor may be attached to the body of the patient to detect and monitor the physiological parameters of the patient. In one implementation, a wearable medical monitor may be disposed about the patient's wrist, and a sensor may be disposed about a finger of the patient and coupled to the wearable medical monitor via a cable. In some situations, the patient may remove the sensor to perform certain tasks, such as eating. However, the sensor may remain tethered to wearable medical monitor via the cable and, as such, may be bothersome to the patient or may interfere with tasks performed by the patient.

SUMMARY

Certain aspects commensurate in scope with the originally claimed embodiments are set forth below. It should be understood that these aspects are presented merely to provide the reader with a brief summary of certain forms the embodiments might take and that these aspects are not intended to limit the scope of the presently disclosed subject matter. Indeed, the full disclosure may encompass a variety of forms that may be similar to or different from the embodiments set forth below.

In a first embodiment, a wearable medical monitor is provided that includes a sensor configured to acquire a physiological signal from a patient. The sensor is configured to be disposed about a finger of the patient. The wearable medical monitor also includes a body portion including a processor configured to receive the physiological signal from the sensor and to determine a physiological parameter of the patient based on the physiological signal. Additionally, the wearable medical monitor includes a cable configured to couple the sensor to the body portion. Further, the wearable medical monitor includes a coupling portion configured to be disposed about a wrist of the patient. The coupling portion includes an attachment member configured to reversibly couple the coupling portion to the body portion of the wearable medical monitor. The attachment member includes a cable retention feature including a channel configured to receive the cable. The cable retention feature is configured to apply a retaining force to the cable when the cable is disposed in the channel.

In a second embodiment, a wearable medical monitor is provided that includes a pulse oximetry sensor configured to be disposed about a finger of a patient. The wearable medical monitor also includes a body portion including a processor configured to receive a physiological signal from the pulse oximetry sensor and to determine a physiological parameter of the patient based on the physiological signal. Additionally, the wearable medical monitor includes a cable configured to couple the pulse oximetry sensor to the body portion. Further, the wearable medical monitor includes a coupling portion configured to be disposed about a wrist of the patient. The coupling portion includes an attachment member configured to reversibly couple the coupling portion to the body portion of the wearable medical monitor. The attachment member includes a base support configured to contact at least a portion of a base surface of the body portion when the body portion is coupled to the coupling portion. The attachment member also includes a first side support extending from a first end of the base support. The first side support is configured to contact at least a portion of a first side surface of the body portion when the body portion is coupled to the coupling portion. The first side support includes a first cable retention feature including a first channel configured to receive the cable. The first cable retention feature is configured to apply a first retaining force to the cable when the cable is disposed in the first channel. Additionally, the attachment member includes a second side support extending from a second end of the base support. The second side support is configured to contact at least a portion of a second side surface of the body portion when the body portion is coupled to the coupling portion. The second side support includes a second cable retention feature including a second channel configured to receive the cable. The second cable retention feature is configured to apply a second retaining force to the cable when the cable is disposed in the second channel In a third embodiment, a device for coupling to a wearable pulse oximeter is provided that includes a strap configured to be disposed about a wrist of a patient. The device also includes an attachment member coupled to the strap. The attachment member is configured to reversibly couple to a wearable pulse oximeter configured to receive signals from a pulse oximetry sensor via a cable. The attachment member includes a base support configured to contact at least a portion of a base surface of the wearable pulse oximeter when the wearable pulse oximeter portion is coupled to the attachment member. The attachment member also includes a first side support extending from a first end of the base support. The first side support is configured to contact at least a portion of a first side surface of the wearable pulse oximeter when the wearable pulse oximeter is coupled to the attachment member. The first side support includes a first cable retention feature including a first channel configured to receive the cable. The first cable retention feature is configured to apply a first retaining force to the cable when the cable is disposed in the first channel Further, the attachment member includes a second side support extending from a second end of the base support. The second side support is configured to contact at least a portion of a second side surface of the wearable pulse oximeter when the wearable pulse oximeter is coupled to the coupling portion.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Provided herein are wearable medical monitors that include cable retention features that may retain or secure a cable coupled to a sensor. For example, a wearable medical monitor may include a body portion coupled to a sensor via a cable. The body portion may include a processor configured to calculate physiological parameters of a patient based on signals received from the sensor. The wearable medical monitor may also include a coupling portion, such as a patient-worn bracelet or strap, which may be configured to couple the wearable medical monitor to a patient. Additionally, the coupling portion may include one or more cable retention features for retaining or securing the cable coupling the sensor to the wearable medical monitor. For example, a patient may insert the cable within a channel of the cable retention feature, and the cable retention feature may be configured to provide a retaining force on the cable to retain or secure the cable within the channel By securing the cable within the channel, movement of the sensor may reduced or minimized when the sensor is removed from the patient. This may allow the patient to reduce or minimize interference of the sensor while the patient performs various tasks, such as eating.

Figure 1:
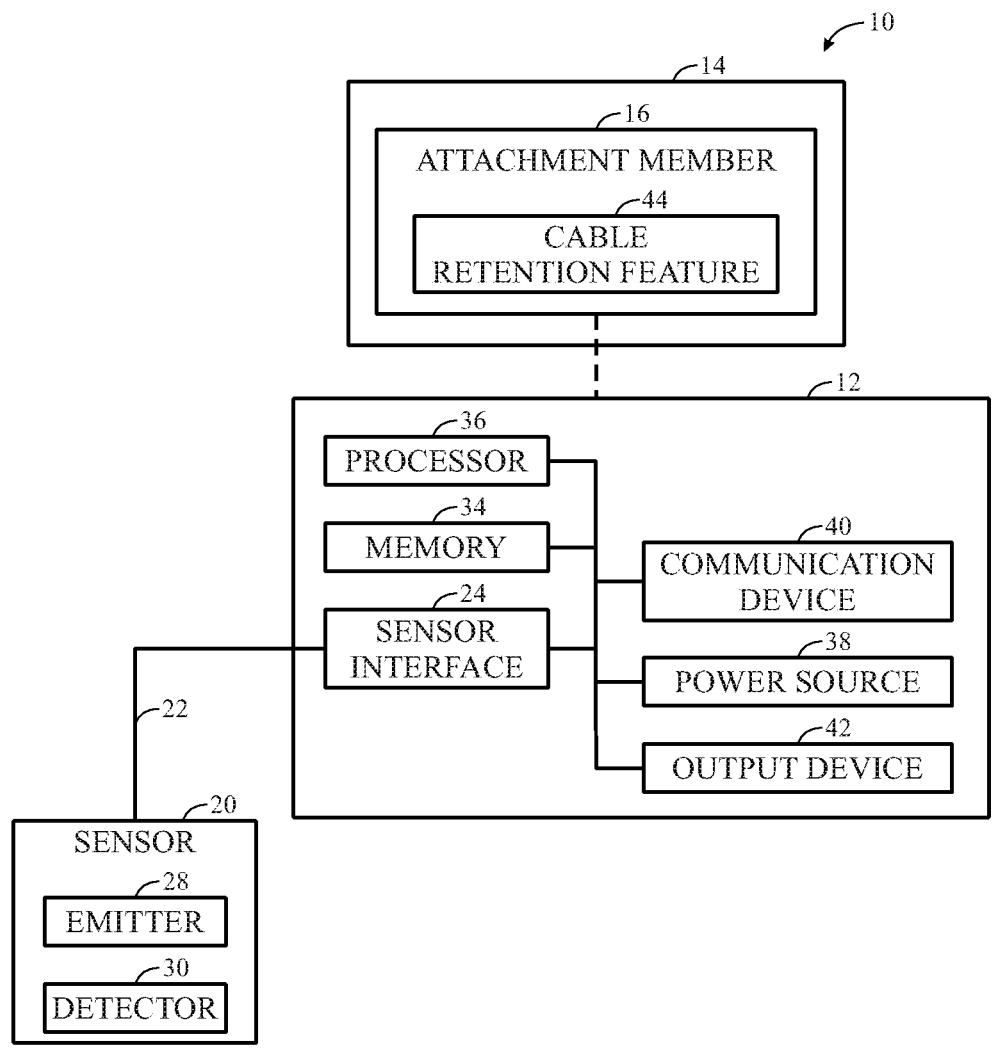
FIG. 1 is a block diagram of a wearable medical monitor including a coupling portion having a cable retention feature, in accordance with an embodiment of the present disclosure.

With the foregoing in mind, FIG. 1 illustrates an embodiment of a wearable medical monitor 10 in accordance with the present disclosure. The wearable medical monitor 10 may include a body portion 12 (e.g., a body, a housing, a pod, an enclosure, a casing, etc.) and a coupling portion 14 (e.g., a mount, a cradle, a base, a harness, an attachment, a support, a patient-coupling portion, a removable portion, etc.). The coupling portion 14 may be reversibly coupled to the body portion 12. For example, the coupling may be facilitated via an attachment member 16 on the coupling portion 14 that reversibly couples to the body portion 12. The coupling portion 14 may be configured to be disposed about and/or secured to a patient. For example, the coupling portion 14 may include a strap, a bracelet, or any other suitable structure that may be configured to wrap around or otherwise attach to a body part of the patient such as, for example, a wrist, an arm, an ankle, the chest, the forehead, or the like.

The wearable medical monitor 10 may be used in conjunction with a medical sensor 20. As illustrated, the wearable medical monitor 10 may be coupled to the medical sensor 20 via a cable 22. In some embodiments, the wearable medical monitor 10 may include a sensor interface 24 configured to receive a sensor connector of the cable 22. In certain embodiments, the medical sensor 20 may be a pulse oximetry sensor configured to acquire pulse oximetry signals. For example, as illustrated, the medical sensor 20 may include at least one emitter 28 and at least one detector 30. The emitter 28 may include at least two light emitting diodes (LEDs), each configured to emit a different wavelength of light, such as red or near infrared light. The detector 30 may be configured to detect light emitted by the emitter 28 after it has passed through tissue of a patient and to generate a physiological signal based on the detected light. While the illustrated embodiment relates to a pulse oximetry sensor, it should be appreciated that the wearable medical monitor 10 may be used in conjunction with a variety of suitable medical sensors 20 to conduct a variety of medical measurements of a patient, including, but not limited to, photoplethysmography, pulse oximetry, regional saturation oximetry, heart rate, ECG, EEG, EMG, glucose/insulin concentration, blood pressure, cerebral autoregulation, respiratory therapy, etc. Accordingly, the medical sensor 20 may be any suitable type of sensor, including, but not limited to, an optical sensor, a pressure sensor, a temperature sensor, a flow rate sensor, a regional oximetry sensor, a heart rate sensor, a blood pressure sensor, an ECG sensor, an EEG sensor, an EMG sensor, a respiratory sensor, etc. Further, the medial sensor 20 may be configured to be placed on a variety of locations on the patient, such as, for example, a finger, the forehead, an ear, a toe, etc. In certain embodiments, the medical sensor 20 may be a flexible, bandage-type sensor that is configured to wrap around a patient's finger or toe. The medical sensor 20 may be reusable, disposable, or may include a combination of reusable and disposable components.

The wearable medical monitor 10 may also include various hardware and/or software components to process the physiological signals received from the medical sensor 20 and to determine physiological parameters of the patient based on the received physiological signals. For example, in embodiments in which the medical sensor 20 is a pulse oximetry sensor, the wearable medical monitor 10 may be configured to determine the oxygen saturation and/or the pulse rate of a patient based on a physiological signal received from the pulse oximetry sensor. In certain embodiments, the wearable medical monitor 10 may include circuitry for processing the physiological signal such as one or more amplifiers, filters, etc. The wearable medical monitor 10 may also include a memory 34 that may store instructions and/or algorithms and a processor 36 that may access and execute the instructions and/or algorithms stored in the memory 34. For example, the processor 36 may execute instructions to control the operation of the medical sensor 20, to receive data and/or physiological signals from the medical sensor 20, and to process the data and/or physiological signals to determine physiological parameters of the patient. In some embodiments, the wearable medical monitor 10 may also include a power source 38, which may be configured to provide power to the wearable medical monitor 10 and/or the medical sensor 20. Additionally, the wearable medical monitor 10 may include a wireless communication device 40 (e.g., a wireless transceiver) to send data to and/or receive data from an external device, such as a medical monitor, a central monitoring station, a laptop, a smart phone, a tablet, or any other suitable processor-based device. Further, the wearable medical monitor 10 may include an output device 42. For example, the output device 42 may include one or more displays (e.g., indicator lights, LCD displays, touchscreens, etc.) and/or one or more speakers to provide outputs related to physiological parameters determined by the wearable medical monitor 10 and/or information relating to the wearable medical monitor 10 (e.g., a power level, a communication status, etc.).

Figure 2:
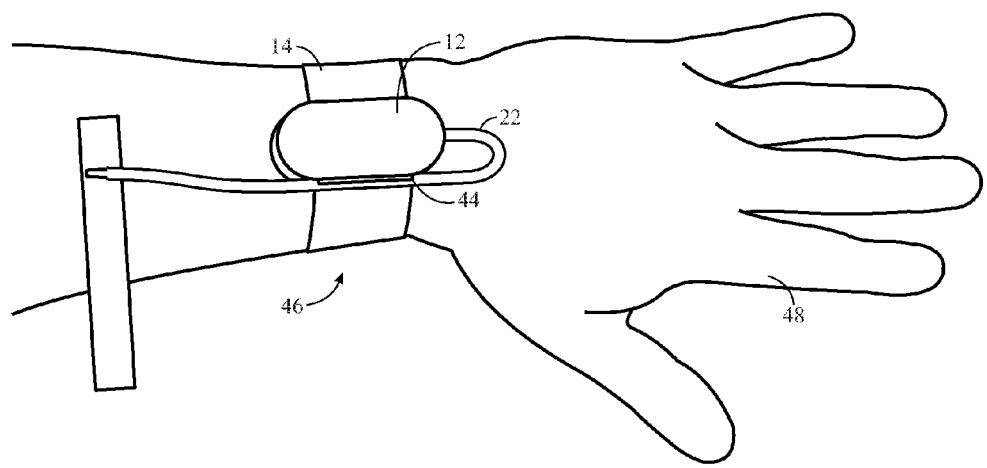
FIG. 2 is a perspective view of a wearable medical monitor including a coupling portion having a cable retention feature that provides a retaining force to a cable coupling a sensor to the wearable medical monitor, in accordance with an embodiment of the present disclosure.

As noted above, the wearable medical monitor 10 may also include one or more cable retention features 44 (e.g., cable mounts, cable fasteners, etc.) configured to retain or secure a cable, such as the cable 22 of the medical sensor 20. As illustrated in FIG. 2, the cable retention feature 44 may be provided on the attachment member 16 of the coupling portion 14 of the wearable medical monitor 10. However, it should be appreciated that in other embodiments, the cable retention feature 44 may be provided on other locations of the coupling portion 14, on the body portion 12, and/or on an additional portion of the wearable medical monitor 10. The cable retention feature 44 may be include suitable securing mechanism, such as slots or channels, tabs, curved tabs, lipped tabs, protrusions, cut-outs, prongs, grooves, loops, snaps, adhesives, hook and loop fasteners, etc. As will be described in more detail below, in certain embodiments, the cable retention feature 44 may include channel configured to receive the cable 22 and the cable retention feature 44 may be configured to apply a retaining force to the cable 22 when the cable 22 is disposed in the channel For example, the cable retention feature 44 may include one or more tabs, protrusions, grooves, and/or prongs that define the channel and provide the retaining force.

In operation, a patient or caregiver may dispose or secure the coupling portion 14 about a wrist 46 of the patient. The patient or caregiver may also dispose the medical sensor 20 about a finger 48 of the patient to enable the wearable medical monitor 10 to receive physiological signals from the patient and to determine physiological parameters of the patient. As noted above, the patient may wish to remove the medical sensor 20 to perform certain tasks. Accordingly, the patient or the caregiver may remove the medical sensor 20 from the finger 48. To reduce or minimize interference of the medical sensor 20 while the patient performs various tasks, the patient or caregiver may secure or retain the cable 22 of the medical sensor 20 using the cable retention feature 44. For example, in certain embodiments, securing or retaining the cable 22 using the cable retention feature 44 may include disposing or inserting the cable 22 within a channel of the cable retention feature 44. As illustrated, the cable 22 may be secured or retained using the cable retention feature 44 such that the medical sensor 20 is kept back from (e.g., a distance away from) the patient's hand. Further, the patient or caregiver may remove the cable 22 from the cable retention feature 44 (e.g., by removing the cable 22 from a channel of the cable retention feature 44) and may dispose the medical sensor 20 about the finger 48 of the patient when the patient has completed the desired tasks and/or when patient monitoring is desired.

Figure 3:
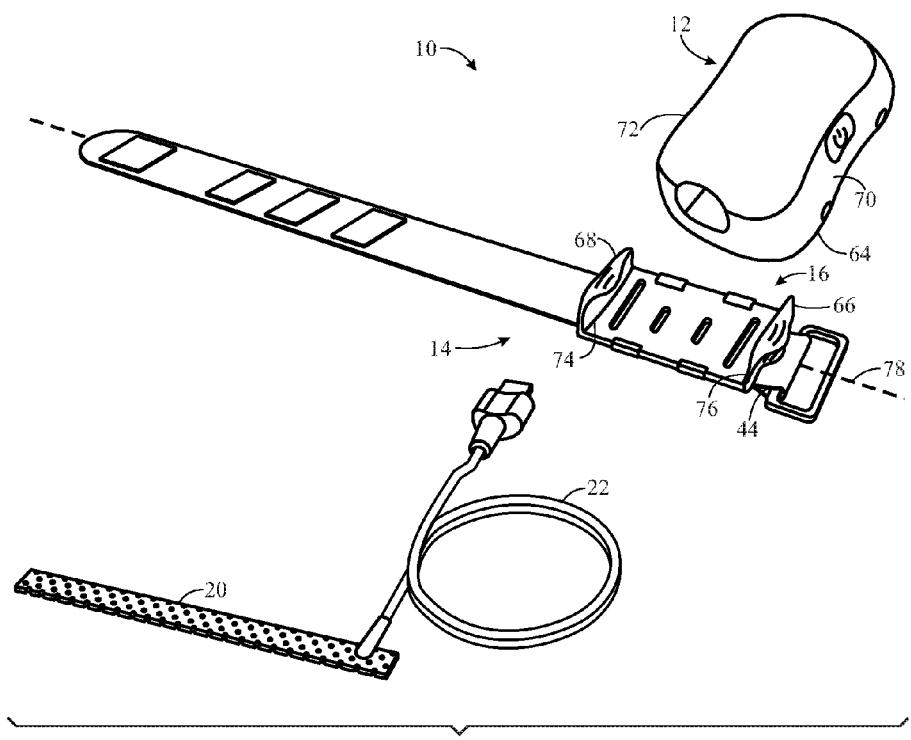
FIG. 3 is a perspective view of a disassembled wearable medical monitor including a body portion, a coupling portion having an attachment member for coupling to the body portion, and a medical sensor, in accordance with an embodiment of the present disclosure.

FIG. 3 illustrates various disassembled components of an embodiment of the wearable medical monitor 10 that includes the body portion 12, the coupling portion 14, and the medical sensor 20 that may couple to the body portion 12 via the cable 22. The coupling portion 14 includes the attachment member 16. As illustrated, the attachment member 16 may include one or more openings 60 (e.g., slots) that may be configured to receive the coupling portion 14 to couple the attachment member 16 to the coupling portion 14. However, it should be noted that the attachment member 16 and/or the coupling portion 14 or may include any suitable features such that the attachment member 16 may be mechanically clipped onto and off of the removable member 14. In other embodiments, the attachment member 16 may be integral with the coupling portion 14.

As noted above, the attachment member 16 may be configured to reversibly couple to the body portion 12. In some embodiments, the attachment member 16 may be sized such that the body portion 12 and the attachment member 16 may be coupled via an interference fit. To facilitate the coupling, the attachment member 16 may be manufactured using flexible materials, such as, for example, polypropylene, polystyrene, or any other suitable soft, molded plastic.

A flexible material may also facilitate the manufacturing of the attachment member 16 in embodiments in which the attachment member 16 includes cut-outs, such as the openings 60. However, in other embodiments, the attachment member 16 may be manufactured using other materials, such as, for example, polycarbonate, polyester, or the like. In some embodiments, the attachment member 16 may include one or more features, such as one or more raised parts (e.g., a protrusion, a flange, or heave) and/or one or more depressed parts (e.g., an opening, a dent, a groove, etc.) that may be configured to couple to one or more complementary features on the body portion 12 to facilitate the reversible coupling of the coupling portion 14 to the body portion 12. Further, the cable retention features 44 and the attachment member 16 may, in certain embodiments, be integrally formed (e.g., molded as one piece).

The attachment member 16 may include a base support 62 (e.g., a base surface) that may contact at least a portion of a base surface 64 of the body portion 12 when the body portion 12 is coupled to the attachment member 16. Additionally, the attachment member 16 may include a first side support 66 (e.g., a first side surface) and a second side support 68 (e.g., a second side surface) that extend vertically from the base support 62. The first and second side supports 66 and 68 may be configured to contact at least a portion of a first side surface 70 and a second side surface 72, respectively, of the body portion 12 when the body portion 12 is coupled to the attachment member 16. As illustrated, the first and second side supports 66 and 68 may be disposed about first and second ends 74 and 76 of the base support 62, respectively, that are generally perpendicular (e.g., between approximately 85 and 95 degrees) to a longitudinal axis 78 of the coupling portion 14. As such, when the coupling portion 14 is disposed about a wrist or an arm of a patient (i.e., the coupling portion 14 is wrapped around the wrist or arm), the first and second side supports 66 and 68 may be generally parallel (e.g., between approximately 175 and 185 degrees) with the longitudinal axis of the arm or the wrist of the patient.

The attachment member 16 may also include the cable retention feature 44, which will be described in more detail below. As illustrated, the cable retention feature 44 may be provided on the first side support 66. In other embodiments, the cable retention feature 44 may be provided on the second side support 68, on both the first and second side supports 66 and 68, or on another portion of the attachment member 16 or the coupling portion 14. For example, if the cable retention feature 44 is provided on the first and second side supports 66 and 68, a patient may have more flexibility in deciding which cable retention arrangement (e.g., outside or inside of the wrist) is more comfortable. It may be desirable to provide the cable retention feature 44 on the first and/or second side supports 66 and 68 so that the cable 22 and/or the medical sensor 20 may also be generally parallel (e.g., between approximately 175 and 185 degrees) with the arm and the wrist of the patient when the cable 22 is secured or retained by the cable retention feature 44. For example, by aligning the cable 22 and/or the medical sensor 20 with the arm and wrist of the patient, the medical sensor 20 may be kept out of the way of the patient's hand and may not interfere with tasks performed by the patient, such as eating.

Figure 4:
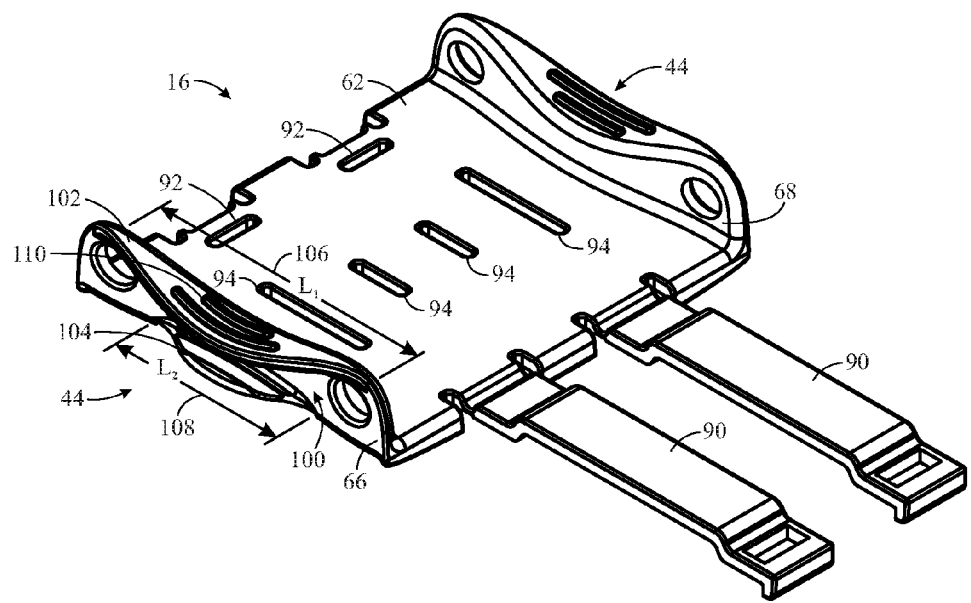
FIG. 4 is a perspective view of an attachment member for a coupling portion including a cable retention feature with two tabs defining a channel, in accordance with an embodiment of the present disclosure.

FIG. 4 illustrates a perspective view of an embodiment of the attachment member 16. In the illustrated embodiment, the attachment member 16 does not include the openings 60, as described above, for coupling to the coupling portion 14, and instead, the attachment member 16 includes two rotatable arms 90 that may clip into two respective openings 92. In this manner, the rotatable arms 90 may rotate around the coupling portion 14 to mechanically clip the attachment member 16 onto and off of the coupling portion 14. The arms 90 may be coupled to the openings 60 via a hinge. Additionally, the attachment member 16 includes openings 94 that may be configured to couple to complementary features (e.g., protrusions) on the body portion 12 to facilitate the reversible coupling of the attachment member 16 to the body portion 12. It should be appreciated that the attachment member 16 may be configured to form an interference fit with the body portion 12 in other embodiments.

The attachment member 16 may also include the base support 62, the first side support 66, and the second side support 68, as described above. As illustrated, the first side support 66 may include the cable retention feature 44. Additionally, the second side support 68 may include the cable retention feature 44. The cable retention feature 44 may be the same or different for the first and second side supports 66 and 68. In the illustrated embodiment, the cable retaining feature 44 includes a channel 100 configured to receive the cable 22. For example, the channel 100 may be sized to fit an outer diameter of the cable 22. As noted above, the cable retaining feature 44 may be configured to apply a retaining force to the cable 22 when the cable 22 is disposed in the channel 100. In particular, the cable retaining feature 44 may also include a first tab 102 (e.g., a first protrusion) and a second tab 104 (e.g., a second protrusion) extending from the first side support 60. The first and second tabs 102 and 104 may define the channel 100 and may provide the retaining force on the cable 22 when the cable 22 is disposed in the channel 100. In certain embodiments, the first tab 102, the second tab 104, and the first side support 66 may define the channel 100 and may provide the retaining force on the cable 22. The first tab 102 may have a first length ($l_1$) 106 and the second tab 104 may have a second length 108 ($l_2$). As illustrated, the first length 106 may be greater than the second length 108. However, in other embodiments, the first length 106 may be the same as or less than the second length 108. Additionally, the first tab 102 may include one or more ridges 110 such that the first tab 102 is easier for a user to grasp and manipulate, for example, to flex the attachment member 16 to facilitate the coupling of the attachment member 16 to the body portion 12.

Figure 5:
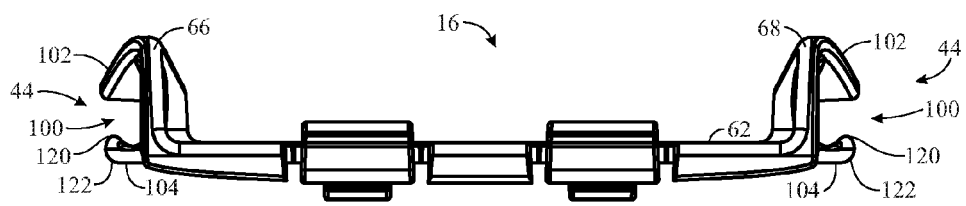
FIG. 5 is a side view of the attachment member of FIG. 4, in accordance with an embodiment of the present disclosure.

FIG. 5 illustrates a side view of the attachment member 16 of FIG. 4. As illustrated, both the first and second side supports 66 and 68 include the cable retention feature 44. It may be desirable to provide the cable retention feature 44 on the first and second side supports 66 and 68 to enable a user to easily secure the cable 22 on either side of the attachment member 16. Additionally, providing the cable retention feature 44 on the first and second side supports 66 and 68 may enable the user to secure two cables to the attachment member 16, which may be desirable if the wearable medical monitor 10 is used in conjunction with two or more medical sensors 20. As illustrated, the cable retention feature 44 is the same on the first and second side supports 66 and 68. In particular, each cable retention feature 44 includes the channel 100, the first tab 102, and the second tab 104. However, as will be described in more detail below, the first and the second side supports 66 and 68 may include different cable retention features 44. In some embodiments, the second tab 104 may include a protrusion 120 (e.g., a bump, a bulge, etc.) that extends into the channel 100. For example, the protrusion 120 may be disposed about an end 122 of the second tab 104 that is distal to the respective side support. The protrusion 120 may facilitate the retention of the cable 22 within the channel 100. Additionally or alternatively, the first tab 102 may include the protrusion 120.

Figure 6:
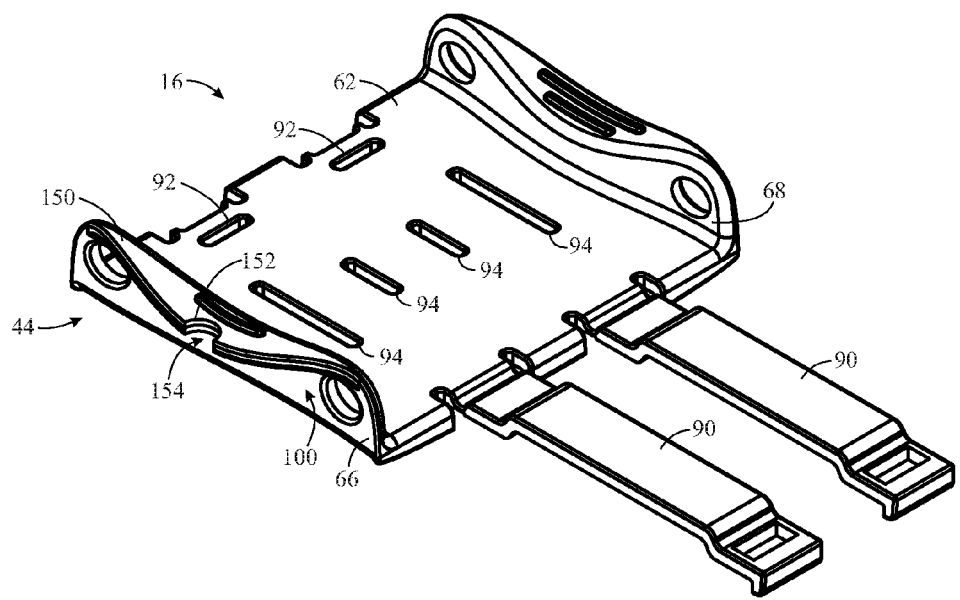
FIG. 6 is a perspective view of an attachment member for a coupling portion including a cable retention feature having a tab with a cut-out defining a channel, in accordance with an embodiment of the present disclosure.
Figure 7:
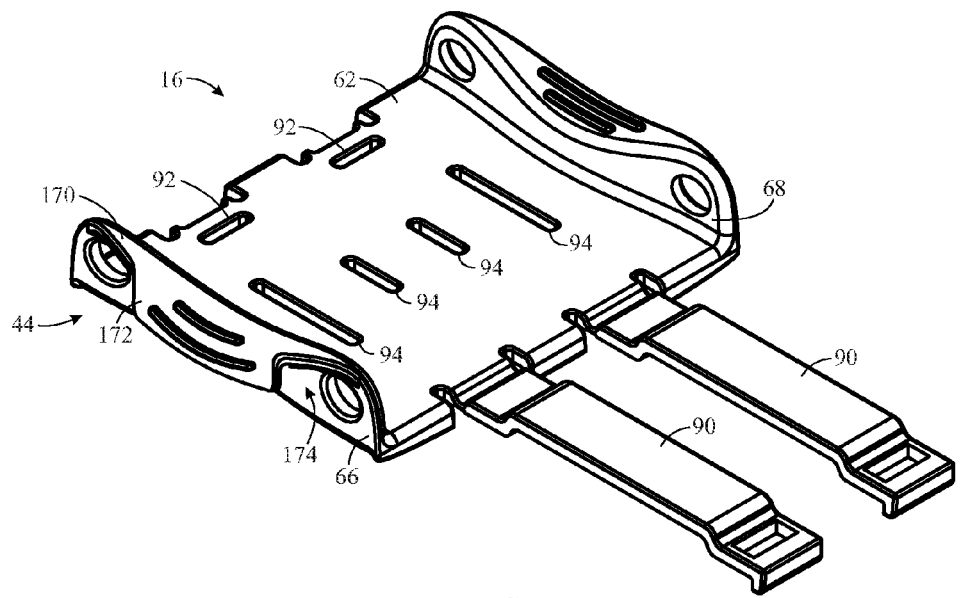
FIG. 7 is a perspective view of an attachment member for a coupling portion including a cable retention feature having a tab with a curved portion defining a channel, in accordance with an embodiment of the present disclosure.
Figure 8:
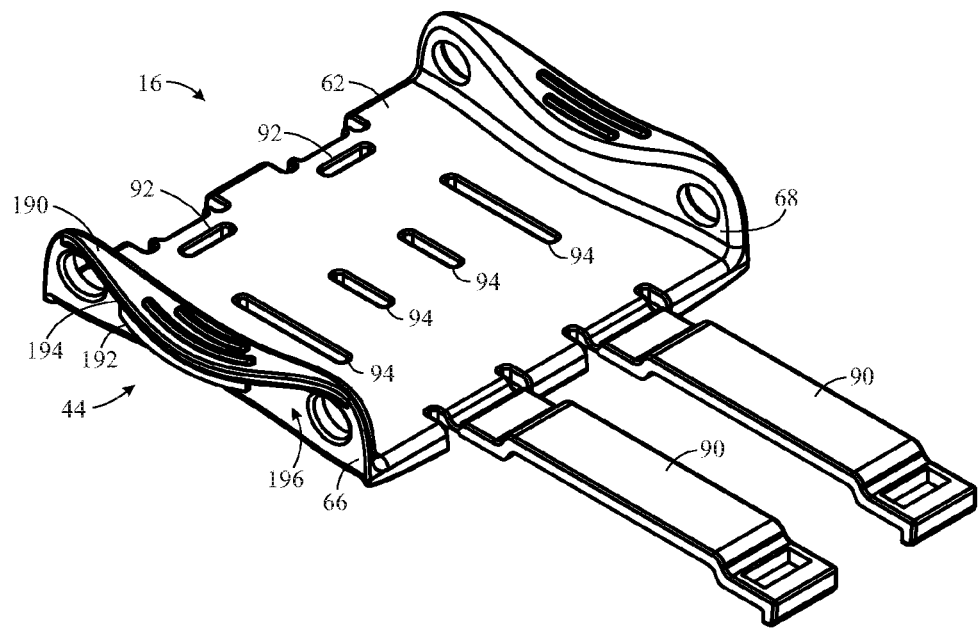
FIG. 8 is a perspective view of an attachment member for a coupling portion including a cable retention feature having a tab with a lip defining a channel, in accordance with an embodiment of the present disclosure.

In other embodiments, the cable retention feature 44 may include a single tab, rather than the first and second tabs 102 and 104. For example, FIG. 6 illustrates an embodiment of the attachment member 16 including the cable retention feature 44 that includes a tab 150 extending from the first side support 66. The tab 150 includes a cut-out 152 defining a channel 154 configured to receive the cable 22. For example, the cut-out 152 may be any suitable shape, such as a circle or a semi-circle, and may be sized to fit about at least a portion of an outer circumference of the cable 22. The cut-out 152 may be configured to apply a retaining force on the cable 22 when the cable 22 is disposed in the channel 152. In other embodiments, the cable retention feature 44 may include a curved tab 152 (e.g., a molded tab) extending from the first side support 66, as illustrated in FIG. 7. For example, the curved tab 170 may include a curved or arcuate portion 172 sized to fit about at least a portion of an outer circumference of the cable 22. In some embodiments, the degree of curvature of the curved portion 172 may be the same as the degree of curvature of the circumference of the cable 22. The curved tab 170 and the curved portion 172 may define a channel 174 configured to receive configured to the cable 22 and may be configured to apply a retaining force on the cable 22 when the cable 22 is disposed in the channel 174. In some embodiments, the curved tab 170, the curved portion 172, and the first side support 66 may define the channel 174 and may provide the retaining force on the cable 22. Further, in some embodiments, the cable retention feature 44 may include a lipped tab 190 extending from the first side support 66, as illustrated in FIG. 8. For example, the lipped tab 190 may include a projecting edge 192 (e.g., a lip). The projecting edge 192 may be disposed at an end 194 of the lipped tab 190 distal to the first side support 66. Additionally, the projecting edge 192 may project toward a channel 196 defined by the projecting edge 192, the lipped tab 190, and the first side support 66. The projecting edge 192, the lipped tab 190, and the first side support 66 may provide a retaining force on the cable 22 when the cable 22 is disposed in the channel 196.

Figure 9:
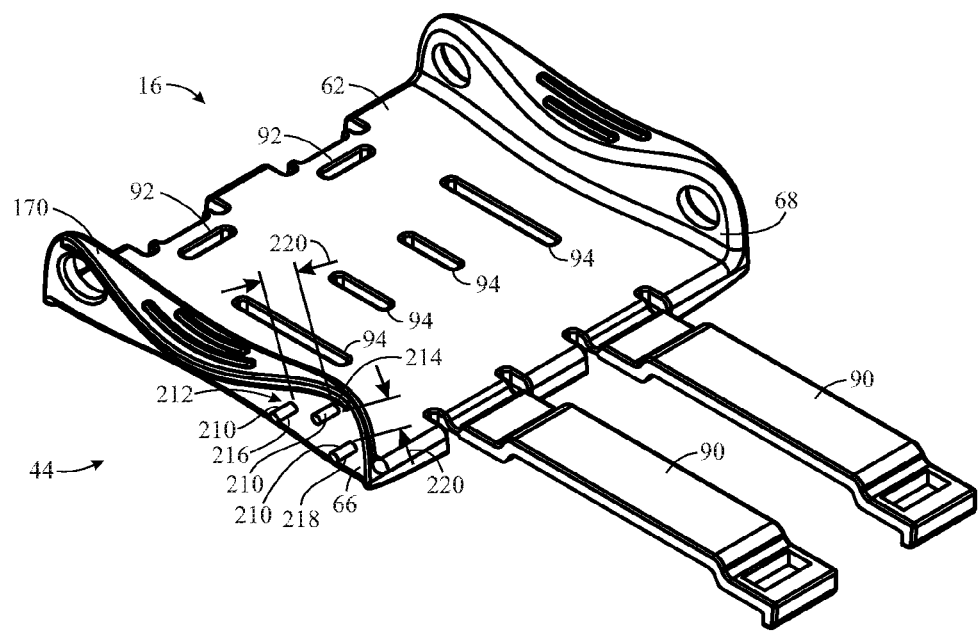
FIG. 9 is a perspective view of an attachment member for a coupling portion including a cable retention feature with a prongs defining a channel, in accordance with an embodiment of the present disclosure.

In other embodiments, the cable retention feature 44 may include at least two prongs (e.g., projections) that define a channel. For example, as illustrated in FIG. 9, the cable retention feature 44 may include three prongs 210 extending from the first side support 66. The three prongs 210 may be arranged on the first side support 66 such that the three prongs 210 define a channel 212 configured to receive the cable 22. For example, the a first prong 214 of the three prongs 210 may be spaced apart from each of a second prong 216 and a third prong 218 of the three prongs 210 by a distance 220 that is approximately equal to an outer diameter of the cable 22. The three prongs 210 may provide a retaining force on the cable 22 when the cable 22 is disposed in the channel 212. Additionally, the three prongs 210 may be any suitable shape, such as cylinders, rectangular prisms, triangular prisms, and the like.

Figure 10:
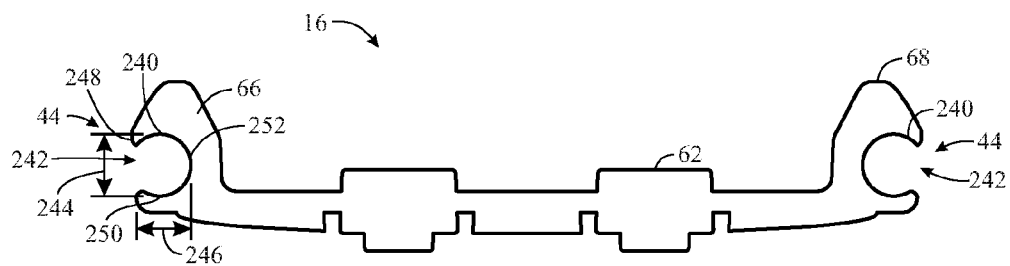
FIG. 10 is a side view of an attachment member for a coupling portion including a cable retention feature with a curved groove defining a channel, in accordance with an embodiment of the present disclosure.

Further, in certain embodiments, the first side support 66 and/or the second side support 68 may be molded or manufactured to form the cable retention feature 44. In particular, the first side supports 66 and/or the second side support 68 may include a curved groove to form the cable retention feature 44. For example, as illustrated in FIG. 10, the cable retention feature 44 may include a curved groove 240 formed in the first side support 66. The curved groove 240 may define a channel 242 configured to receive the cable 22 and may provide a retaining force on the cable 22 when the cable 22 is disposed in the channel 242. The curved groove 240 may include a height 244 that varies along a length 246 of the first side support 66. For example, the height 244 may increase (e.g., continuously increase) from a distal end 248 of the first side support 66 to an intermediate point 250 (e.g., a midpoint along the length 246) of the first side support 66. Additionally, the height 244 may decrease (e.g., continuously decrease) from the intermediate point 250 to a proximal end 252 of the first side support 66. The curved groove 240 may be sized to fit about at least a portion of an outer circumference of the cable 22. For example, the height 244 at the intermediate point 250 may be approximately equal to an outer diameter of the cable 22. Additionally, as illustrated, the second side support 68 may also include the curved groove 240 that defines the channel 242 configured to receive the cable 22.

Figure 11:
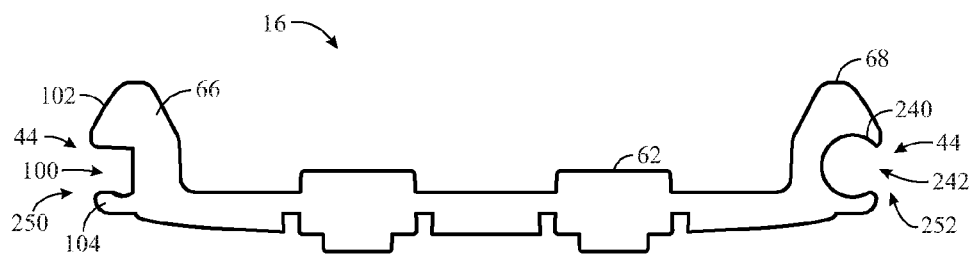
FIG. 11 is a side view of an attachment member for a coupling portion including two different cable retention features.

As noted above, in certain embodiments, the attachment member 16 may include different cable retention features 44 on the first and second side supports 66 and 68. For example, as illustrated in FIG. 11, the first side support 66 may include a first cable retention feature 250 and the second side support 68 may include a second cable retention feature 252 that is different from the first cable retention feature 250 (e.g., different sizes or shapes, accommodates different types of sensors, etc.). As illustrated, the first cable retention feature 250 may include the first and second tabs 102 and 104 defining the channel 100, as described above in FIG. 5. Additionally, the second cable retention feature 252 may include the curved groove 240 defining the channel 242, as described above in FIG. 10. However, it should be appreciated that the first and second cable retention features 250 and 252 may include any suitable features, such as the features described herein, in any suitable combination.

Figure 12:
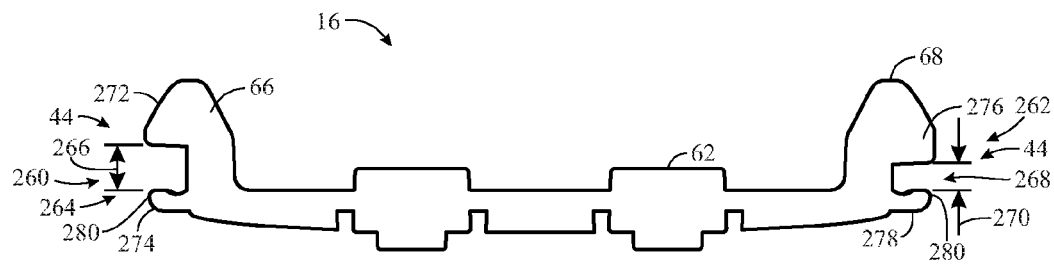
FIG. 12 is a side view of an attachment member for a coupling portion including a first cable retention feature configured to retain a first cable with a first outer diameter and a second cable retention feature configured to retain a second cable with a second outer diameter.

In other embodiments, the attachment member 16 may include different cable retention features 44 configured to retain different sized cables 22 (e.g., different outer diameters). This may be desirable in embodiments in which the wearable medical monitor 10 is operated in conjunction with different types of medical sensors 20. For example, as illustrated in FIG. 12, the first side support 66 may include a first cable retention feature 260 configured to retain a first cable with a first outer diameter, and the second side support 68 may include a second cable retention feature 262 configured to retain a second cable with a second outer diameter. In particular, the first cable retention feature 260 may include a first channel 264 configured to receive the first cable, and the first channel 264 may have a first height 266 sized according to (e.g., approximately equal to) the first outer diameter of the first cable. Additionally, the second cable retention feature 262 may include a second channel 268 configured to receive the second cable, and the second channel 268 may have a second height 270 sized according to (e.g., approximately equal to) the second outer diameter of the second cable. It should be appreciated that the first and second cable retention features 260 and 262 may include the same features (e.g., tabs, prongs, curved grooves, cut-outs, curved tabs, lipped tabs, etc.) or different features. For example, in the illustrated embodiment, the first cable retention feature 260 may include a first tab 272 and a second tab 274 defining the first channel 264, and the second cable retention feature 262 may include a first tab 276 and a second tab 278 defining the second channel 268. Further, in some embodiments, the second tab 274 and the second tab 278 may each include a protrusion 280 that extends into the respective channel.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, it should be understood that elements of the disclosed embodiments may be combined or exchanged with one another.

What is claimed is:

1. A wearable medical monitor, comprising:
   a sensor attachable to a finger of a patient;
   a housing comprising a processor configured to receive a physiological signal from the sensor and to determine a physiological parameter of the patient based on the physiological signal;
   a cable comprising a connector that couples the sensor to the housing; and
   a mount removably attachable to the housing to secure the housing about a wrist of the patient, wherein the mount comprises a channel positioned on the mount to receive the cable into the channel and a cable fastener positioned about the channel to retain the cable in the channel.

2. The wearable medical monitor of claim 1, wherein the sensor comprises a pulse oximetry sensor, and the physiological parameter comprises oxygen saturation.

3. The wearable medical monitor of claim 1, wherein the mount comprises a base support and first and second side supports extending vertically from the base support, wherein the first and second side supports are spaced to contact the housing between them.

4. The wearable medical monitor of claim 3, wherein the first side support comprises the channel and the cable fastener.

5. The wearable medical monitor of claim 4, wherein the cable fastener comprises first and second tabs extending from the first side support, wherein the channel is defined by at least the first and second tabs.

6. The wearable medical monitor of claim 5, wherein the first tab comprises a protrusion that extends into the channel.

7. The wearable medical monitor of claim 5, wherein the first tab comprises a first length and the first side support comprises a second length, and the first length is less than the second length.

8. The wearable medical monitor of claim 4, wherein the first side support comprises a curved groove, and the channel is defined by the curved groove.

9. The wearable medical monitor of claim 4, wherein the cable fastener comprises at least two prongs protruding from the first side support, and wherein the channel is defined by at least a space between the at least two prongs.

10. The wearable medical monitor of claim 4, wherein the cable fastener comprises a tab extending from the first side support, and wherein the tab comprises a cut-out sized to fit about a portion of an outer circumference of the cable and the channel is defined by at least the cut-out.

11. The wearable medical monitor of claim 4, wherein the cable fastener comprises a tab extending from the first side support, and wherein the tab comprises an arcuate portion sized to fit about a portion of an outer circumference of the cable and the channel is defined by at least the arcuate portion.

12. The wearable medical monitor of claim 4, wherein the cable fastener comprises a tab extending from the first side support, and wherein the tab comprises a projecting edge disposed at an end of the tab distal to the first side support and the channel is defined by at least the tab and the projecting edge.

13. The wearable medical monitor of claim 4, wherein the first and second side supports are configured to be generally parallel with the patient's wrist when the mount is disposed about the patient's wrist.

14. The wearable medical monitor of claim 1, wherein the mount comprises a bracelet or a strap sized to encircle a wrist.

15. The wearable medical monitor of claim 3, wherein the mount comprises a second channel positioned on the mount to receive the cable into the second channel and a second cable fastener positioned about the second channel to retain the cable in the second channel, and wherein the first side support comprises the cable fastener and the channel and the second side support comprises the second cable fastener and the second channel.

16. A wearable medical monitor, comprising:
    a photoplethysmography sensor configured to be disposed about a finger of a patient;
    an enclosure comprising a processor configured to receive a photoplethysmograph signal from the photoplethysmography sensor and to determine a physiological parameter of the patient based on the photoplethysmograph signal;
    a cable comprising a connector that couples the photoplethysmograph sensor to the enclosure; and
    a wrist strap comprising:
      a base support configured to contact at least a portion of a base surface of the enclosure when the enclosure is coupled to the wrist strap;
      a first side support extending from a first end of the base support, wherein the first side support is configured to contact at least a portion of a first side surface of the enclosure when the enclosure is coupled to the wrist strap, and wherein the first side support comprises a first channel sized to receive and retain the cable; and
      a second side support extending from a second end of the base support, wherein the second side support is configured to contact at least a portion of a second side surface of the enclosure when the enclosure is coupled to the wrist strap, and wherein the second side support comprises a second channel sized to receive and retain the cable.

17. The wearable medical monitor of claim 16, wherein the first side support comprises a first cable fastener positioned about the first channel and configured to apply a first retaining force to the cable when the cable is disposed in the first channel.

18. The wearable medical monitor of claim 16, wherein the first side support comprises first and second tabs that extend from the first side support and are positioned about the first channel to retain the cable in the first channel, and wherein the second side support comprises third and fourth tabs that extend from the second side support and are positioned about the second channel to retain the cable in the second channel.

19. The wearable medical monitor of claim 18, wherein the first tab comprises a first protrusion extending into the first channel and the third tab comprises a second protrusion extending into the second channel.

20. A wearable medical monitor, comprising;
    a strap configured to be disposed about a wrist of a patient;

a pulse oximeter comprising a processor programmed to receive and process physiological signals from a patient;

a cradle coupled to the strap, wherein the cradle is configured to reversibly couple to the pulse oximeter, wherein the cradle comprises:

a base support configured to contact at least a portion of a base surface of the pulse oximeter when the pulse oximeter is coupled to the cradle;

a first side support extending from a first end of the base support, wherein the first side support is configured to contact at least a portion of a first side surface of the pulse oximeter when the pulse oximeter is coupled to the cradle, and wherein the first side support comprises a first cable fastener comprising a first channel sized to receive a cable, wherein the first cable fastener is configured to apply a first retaining force to the cable when the cable is disposed in the first channel; and a second side support extending from a second end of the base support, wherein the second side support is configured to contact at least a portion of a second side surface of the pulse oximeter when the pulse oximeter is coupled to the cradle.

21. The wearable medical monitor of claim 20, wherein the first cable fastener comprises first and second tabs extending from the first side support, and the first channel is defined by at least the first and second tabs, and wherein the first tab comprises a protrusion extending into the first channel.

22. The wearable medical monitor of claim 20, wherein the second side support comprises a second cable fastener comprising a second channel configured to receive the cable, wherein the second cable fastener is configured to apply a second retaining force to the cable when the cable is disposed in the second channel.

23. The wearable medical monitor of claim 20, comprising:

a photoplethysmography sensor comprising an emitter and a detector to acquire the physiological signals; and a patient cable comprising a connector that couples the photoplethysmography sensor to the pulse oximeter;

wherein the first channel is sized to receive the patient cable and the first cable fastener is configured to apply the first retaining force to the patient cable when the patient cable is disposed in the first channel.

* * * * *